United States Patent [19]
Knudson

[11] Patent Number: 5,146,091
[45] Date of Patent: Sep. 8, 1992

[54] BODY FLUID CONSTITUENT MEASUREMENT UTILIZING AN INTERFERENCE PATTERN

[75] Inventor: Mark B. Knudson, Shoreview, Minn.
[73] Assignee: Inomet, Inc., Roseville, Minn.
[21] Appl. No.: 621,771
[22] Filed: Dec. 4, 1990

Related U.S. Application Data

[63] Continuation-in-part of Ser. No. 510,935, Apr. 19, 1990.

[51] Int. Cl.[5] ............................................. G01N 33/48
[52] U.S. Cl. .................................... 250/341; 128/633; 128/664; 356/39
[58] Field of Search ............... 356/41, 39; 250/341; 128/633, 664

[56] References Cited

U.S. PATENT DOCUMENTS

| | | | |
|---|---|---|---|
| 2,414,747 | 1/1947 | Kirschbaum | 128/142 |
| 3,054,397 | 9/1962 | Benzinger | 128/2 |
| 3,054,893 | 9/1962 | Dasburg | 246/182 |
| 3,156,117 | 11/1964 | Benzinger | 73/359 |
| 3,282,106 | 11/1966 | Barnes | 73/355 |
| 3,463,142 | 8/1969 | Harte | 128/2 |
| 3,825,342 | 7/1974 | Lubbers et al. | 356/41 |
| 3,878,836 | 4/1975 | Twentier | 128/9 |
| 3,949,740 | 4/1976 | Twentier | 128/9 |
| 3,958,560 | 5/1976 | March | 128/2 |
| 4,014,321 | 3/1977 | March | 128/2 |
| 4,086,915 | 5/1978 | Kofsky et al. | 128/2 |
| 4,169,676 | 10/1979 | Kaiser | 356/39 |
| 4,195,641 | 4/1980 | Johnes et al. | 128/632 |
| 4,223,680 | 9/1980 | Jobsis | 128/633 |
| 4,281,646 | 8/1981 | Kinoshita | 128/6 |
| 4,344,438 | 8/1982 | Schultz | 128/634 |
| 4,407,290 | 10/1983 | Wilber | 128/633 |
| B1 4,407,290 | 10/1986 | Wilber | 128/633 |
| 4,427,889 | 1/1984 | Muller | 250/339 |
| 4,575,237 | 3/1986 | Suzuki | 356/1 |
| 4,602,642 | 7/1986 | O'Hara et al. | 128/664 |
| 4,622,974 | 11/1986 | Coleman et al. | 128/634 |
| 4,655,225 | 4/1987 | Dahne et al. | 128/633 |
| 4,662,360 | 5/1987 | O'Hara et al. | 128/664 |
| 4,685,463 | 8/1987 | Williams | 128/632 |
| 4,704,029 | 11/1987 | Van Henvelen | 356/39 |
| 4,750,830 | 6/1988 | Lee | 361/211 |
| 4,772,561 | 9/1988 | Genshaw | 436/169 |
| 4,790,324 | 12/1988 | O'Hara et al. | 128/664 |
| 4,800,886 | 1/1989 | Nestor | 128/634 |
| 4,805,623 | 2/1989 | Jöbsis | 356/41 |
| 4,850,365 | 7/1989 | Rosenthal | 128/664 |
| 4,854,699 | 8/1989 | Edgar, Jr. | 356/41 |
| 4,882,493 | 11/1989 | Schlager | 250/346 |
| 4,926,867 | 5/1990 | Kanda et al. | 128/633 |

FOREIGN PATENT DOCUMENTS

| | | |
|---|---|---|
| 0160768 | 11/1985 | European Pat. Off. . |
| 381608 | 8/1990 | European Pat. Off. . |
| 3619442 | 12/1987 | Fed. Rep. of Germany . |
| 3901749 | 10/1990 | Fed. Rep. of Germany . |
| 1526973 | 1/1967 | France . |
| WO A8911825 | 12/1989 | PCT Int'l Appl. . |
| 2033575A | 5/1980 | United Kingdom . |
| 2055476 | 3/1981 | United Kingdom . |

OTHER PUBLICATIONS

Sep., 1987 paper from the ISAO-ESAO Joint Meeting Entitled, "Blood Glucose Measurement by Infrared Spectroscopy", by Zeller.

Article entitled, "Determination of Physiological Levels of Glucose in an Aqueous Matrix with Digitally Filtered Fourier Transform Near-Infrared Spectra", by Arnold et al., published in *Analytical Chemistry*, vol. 92, No. 14, Jul. 17, 1990.

Paper entitled, "Blood/Glucose Measurement by Multiple Attenuated Total Reflection and Infrared Absorption Spectroscopy", from the IEEE Transactions on Biomedical Engineering, vol. 37, No. 5, May 1990.

*Primary Examiner*—Carolyn E. Fields
*Assistant Examiner*—James E. Beyer
*Attorney, Agent, or Firm*—Merchant, Gould, Smith, Edell, Welter & Schmidt

[57] ABSTRACT

An apparatus is disclosed for measuring a body fluid constituent. In a preferred embodiment, the apparatus directs light against a tissue containing the constituent and detects an amount of light absorption in a reflected light from said tissue. The amount of absorption is analyzed to determine the amount of constituent in the blood within the tissue.

12 Claims, 3 Drawing Sheets

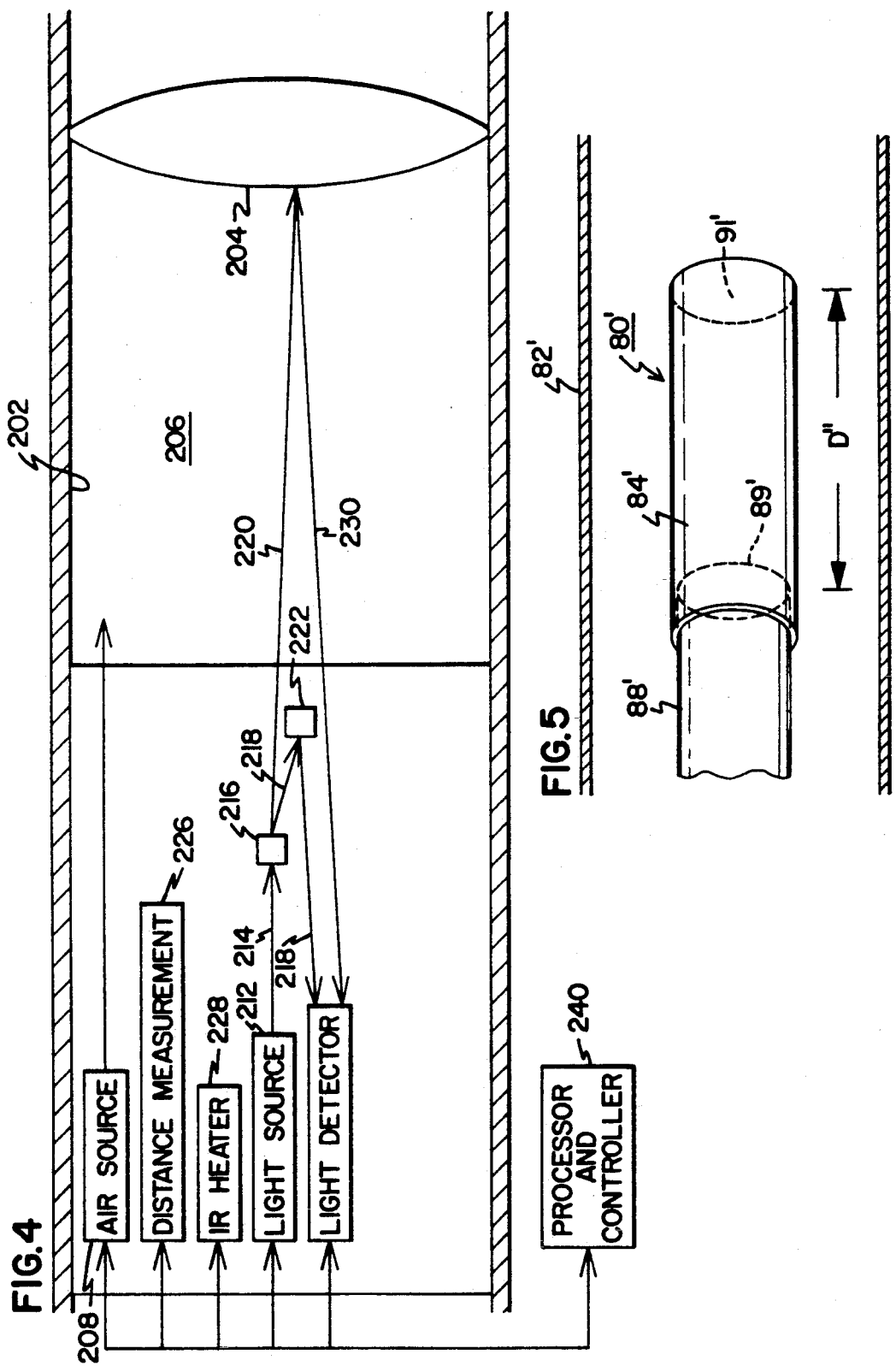

BODY FLUID CONSTITUENT MEASUREMENT UTILIZING AN INTERFERENCE PATTERN

I.

CROSS REFERENCE TO RELATED APPLICATIONS

The present application is a continuation-in-part application of my earlier filed and commonly assigned, copending U.S. patent application Ser. No. 07/510,935 filed Apr. 19, 1990 and entitled "INFRARED AND NEAR-INFRARED TESTING OF BLOOD CONSTITUENTS," and the present application disclose certain material which is claimed in concurrently and commonly assigned filed U.S. patent application Ser. No. 621,823, entitled "INVASIVE FTIR BLOOD CONSTITUENT TESTING," of which I am a co-inventor.

II.

BACKGROUND OF THE INVENTION

1. Field of the Invention

This patent application pertains to an apparatus for testing blood constituents. More particularly, this application pertains to such an apparatus utilizing spectrophotometric analysis of blood constituents.

2. Description of the Prior Art

The use of spectrophotometric methods to quantitatively determine the concentration of a blood constituent are known. For example, U.S. Pat. No. 4,882,492 to Schlager teaches a non-invasive near-infrared measurement of blood analyte concentrations. The Schlager patent is particularly directed to the measurement of blood glucose levels. The Schlager patent recognizes that certain wavelengths of light in the near-infrared spectrum are absorbed by glucose. Modulated light is directed against a tissue (shown as an earlobe). The light is either passed through the tissue or impinged on a skin surface. The light is spectrally modified in response to the amount of analyte (for example, glucose) in the blood and tissue. The spectrally modified light is split with one beam passed through a correlation cell. The other beam is passed through a reference cell. The intensity of the beams passing through the correlation cell and the reference cell are compared to calculate a glucose concentration in the sample.

U.S. Pat. No. 4,805,623 to Jobsis teaches a spectral photometric method for quantitatively determining the concentration of a component in human blood. The Jobsis method teaches various steps including the determination of an apparent effective path length for the light which is being absorbed by the constituent being measured.

U.S. Pat. No. 4,655,225 to Dahne et al. teaches a spectrophotometric method and apparatus for non-invasive testing. The Dahne patent is particularly directed to the measurement of blood glucose.

U.S. Pat. Nos. 4,014,321 and 3,958,560 to March teach non-invasive glucose sensor systems which involve passing light through the cornea of the patient.

U.S. Pat. No. 4,427,889 to Muller, dated Jan. 24, 1984, teaches a method and apparatus for molecular spectroscopy. In the embodiment described within the patent, blood glucose is determined through absorption analysis of infrared wavelengths absorbed in a glucose-containing sample (such as whole blood or urine).

Notwithstanding the developments in the art, a need for an improved spectrophotometric measurement apparatus and method persists. For example, systems and methods which require the calculation of an apparent light pathway are susceptible to inaccuracy. Such a system is shown in the aforementioned U.S. Pat. No. 4,805,623. Systems which have fixed dimensioned light pathways (for example, U.S. Pat. No. 4,014,321) are restricted in their use and practicality. It is also desirable to develop a system and apparatus which can be used for non-invasive testing as well as invasive testing (for example, as a continuous monitor for testing blood glucose level during surgery or insulin treatment). Further, it is desirable to develop a system which can be used in conjunction with a chemical emission system (such as a blood glucose monitoring system which controls an insulin administering apparatus).

In addition to the foregoing, it is desirable to provide an apparatus which can perform multiple wavelength analysis (i.e., broad spectrum analysis) of a sample. A common technique for providing a broad spectrum analysis is a so-called Fourier transform infrared ("FTIR") spectrometer. Such spectrometers are well known in the art and include means for generating a beam of a source light. The beam is then split by a beam splitter into a reference light and a test light. The reference light is reflected off of a fixed mirror to a light detector. The test light is passed through or reflected from a sample and off a moving mirror. The moving mirror translates the information from the frequency domain to the time domain to produce an interferogram. When passed through the sample, various frequencies of the light are absorbed at various rates depending upon the constituents of the sample. The light from the reflected test beam is directed to the light detector where it crosses paths with the reference beam. The modified test beam and the reference beam interact to form an interference pattern which is detected by the light detector and processed through a processor to generate a signal indicative of the constituents in the sample.

The use of Fourier transformed infrared spectrometry (FTIR) in testing for blood constituents (such as blood glucose) is known. A description of such a test is described in a paper entitled "Determination of Physiological Levels of Glucose in an Aqueous Matrix with Digitally Filtered Fourier Transform Near-Infrared Spectra" by Mark A. Arnold and Garry W. Small of the Department of Chemistry, University of Iowa, Iowa City, Iowa, as published in *Analytical Chemistry*, Vol. 62, No. 14, Jul. 15, 1990.

In prior FTIR analysis, the test sample (such as a volume of blood) would be removed from a patient and placed on a FTIR spectrometer. As a result, the test was invasive as well as non-continuous.

It is an object of the present invention to provide a technique for using FTIR spectrometry to test for blood constituents in a manner which can be both continuous and non-invasive.

III.

SUMMARY OF THE INVENTION

According to preferred embodiment of the present invention, an apparatus is disclosed for determining a level of a constituent such as glucose in a body fluid such as blood. The apparatus includes FTIR spectrome-

IV.
BRIEF DESCRIPTION OF THE DRAWINGS

FIG. 4 is a schematic view of an apparatus according to the present invention for use in measuring a constituent in a tympanic membrane where the tympanic membrane is utilized as a moving mirror in an FTIR spectrometer arrangement; and FIG. 5 is a view of an invasive FTIR system.

IV.
DESCRIPTION OF A PREFERRED EMBODIMENT

A. Non-FTIR Spectrometry

Figure 1:
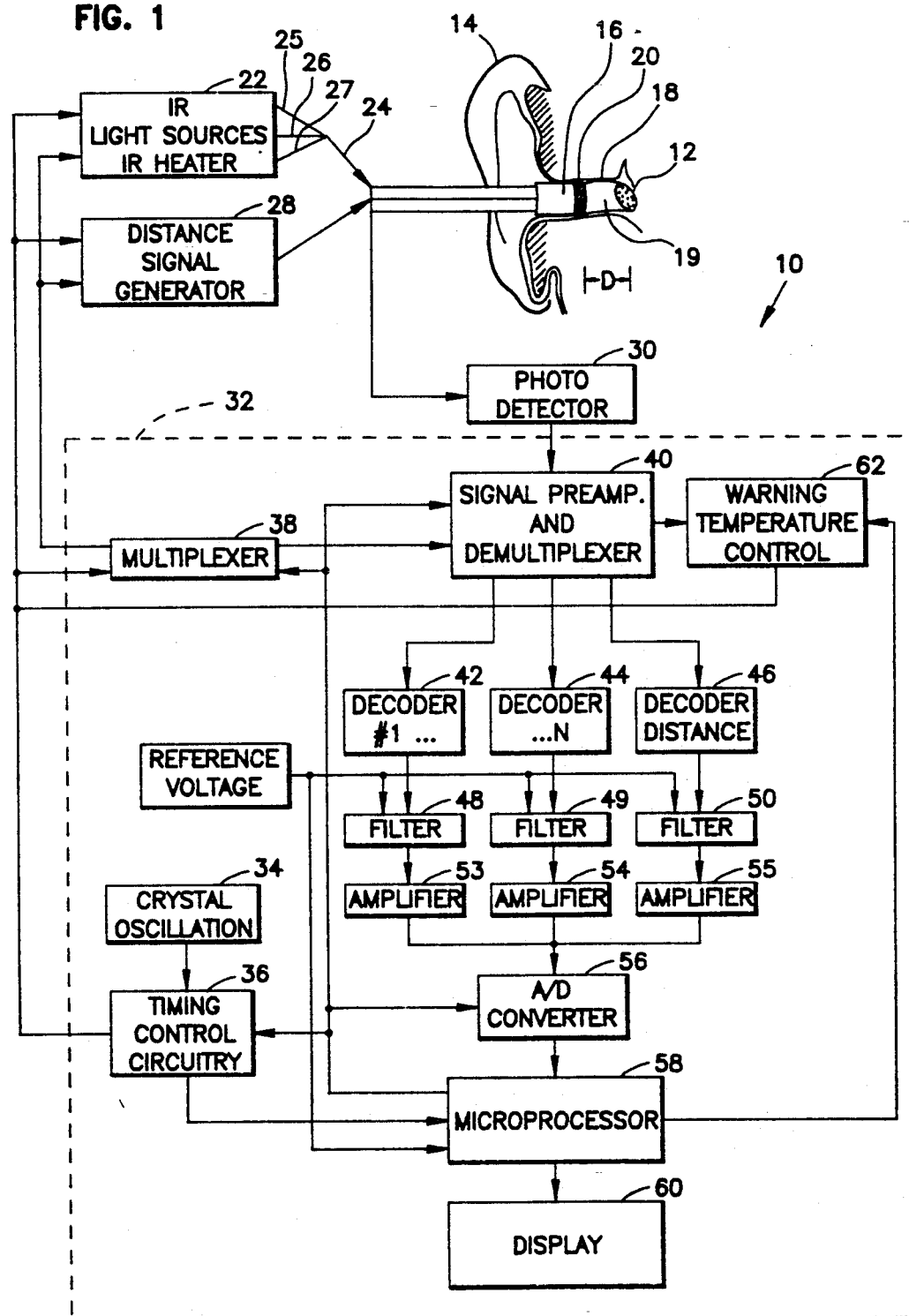
FIG. 1 is a schematic representation of an apparatus of showing its use in an embodiment for measuring a constituent within the tissues, tissue fluid and blood vessels in a tympanic membrane.

Referring now to FIG. 1, an apparatus is shown for use in non-invasive testing for a particular body fluid constituent—namely, blood glucose. Also, in FIG. 1, the apparatus is shown in use for measuring glucose in body fluid in a tympanic membrane. While the illustrated application is a preferred embodiment, it will be appreciated that the salient features are applicable to a wide variety of body constituents. For example, glucose as well as other body constituents could be measured in a plurality of body fluids such as blood, tissue (intestitial) fluid, crevicular fluid, and peritoneal fluid.

In FIG. 1, the apparatus 10 is shown in use for measuring glucose within body fluid in of a tympanic membrane 12 in a human ear 14. (The apparatus 10 is also suitable for veterinary uses.) In the embodiment now being described, the apparatus 10 is non-invasive (i.e., no penetration of body tissue is required).

The apparatus 10 includes a distal end which carries a speculum 16. Speculum 16 is preferably disposable and is sized to be received within the auditory canal 18 of an ear 14. The speculum is selected to block the auditory canal 18 to prevent ambient light from entering the ear past the speculum 16. Accordingly, the speculum 16 closes the auditory canal 18 to define a closed testing volume 19 between the speculum 16 and the tympanic membrane 12. The actual distance D between the source of light in the speculum 16 and the tympanic membrane 12 will vary with each use of the apparatus 10. However, as will be more fully described, the apparatus 10 includes means for measuring the distance D.

For reasons that will become apparent, the speculum 16 has a tip 20 which opposed the tympanic membrane 12 upon insertion of the speculum into the auditory canal 18. The tip 20 is selected to pass certain predetermined light wavelengths (e.g. wavelengths which are absorbable by constituents which are to be measured).

In a preferred example of measuring glucose within the tympanic membrane 12, the tip 20 is selected to pass infrared and near-infrared light wavelengths. It will be appreciated that a speculum such as speculum 16 having an infrared and near-infrared transparent tip 20 is known in the art. An example of such is shown in U.S. Pat. No. 4,662,360. Such prior art speculums have been developed for use with tympanic thermometers. The speculums of such thermometers would be inserted within the auditory canal and would permit infrared radiation generated by a tympanic membrane to pass through the tip of the speculum toward infrared radiation detecting apparatus contained within the speculum. With such prior art apparatus, a healthcare provider can measure body temperature by detecting infrared radiation emitted from the tympanic membrane. Examples of complete apparatus for measuring body temperature from the tympanic membrane are shown in U.S. Pat. Nos. 4,602,642; 3,949,740; 3,878,836 and 4,790,324.

The present technique contemplates the generation of a testing light which includes a wavelength absorbable by the constituent to be measured (for example, blood glucose). Shown schematically in FIG. 1, the system includes a generator 22 of broad band light sources including near-infrared and infrared light sources. Generator 22 may be a lasing diode or a broad band light source with filters.

The generator 22 is selected to generate a testing light of known intensity which includes a wavelength(s) absorbable by the constituent to be tested. The generator 22 also includes means for generating one or more reference lights of known intensity having a wavelength which is not absorbable by the constituent to be measured. Also, for reasons that will be described, the generator 22 includes means for generating infrared radiation of a heating wavelength selected to be directed for the purpose of warming and controlling the temperature of the tympanic membrane 12 and volume 19.

A waveguide 24 (e.g., a fiber optic cable or light directing tube) is passed from the generator 22 into the speculum 16 to be directed toward and oppose the tympanic membrane 12 upon insertion of the speculum 16 into the auditory canal 18. An alternative to using waveguide 24 would be for the generator 22 to be a light source (e.g., a diode or a tungsten filament) within the speculum 16.

The reader will note that the wavelengths of the testing light, the reference light and the infrared heating radiation will all be passed by tip 20 toward tympanic membrane 12. In the preferred embodiment, the testing light will include a glucose sensitive wavelength in a region bounded by approximately 500 to about 4000 wave numbers (cm$^{-1}$) The non-absorbable reference light will have a preferred wavelength in about the same wavelength range (e.g. an absorbable wavelength in the range of 1030-1050 wave numbers and a non-absorbable wavelength of about 1150 wave numbers).

If it is desirable to test for constituents in addition to glucose, the generator 22 is simply selected to generate additional wavelengths selected for their absorbability by the desired constituent. In the schematic representation of FIG. 1, three optical paths 25-27 are shown for directing the infrared and near-infrared radiation toward the tympanic membrane 12. In a preferred embodiment, all light signals will be passed through a waveguide 24 with the light signals detected at a single detector.

Including being coupled to light generator 22, the speculum 16 is coupled with a distance signal generator 28. Distance signal generator 28 includes means for generating a signal for use in measuring the distance D from the speculum 16 to the tympanic member 12. In one embodiment, the distance signal generator 28 is an ultrasonic generator which will measure the distance D through Doppler measurements. However, the present technique need not be limited to such an embodiment. For example, light distance measuring techniques can also be employed. In such a case, the functions of generators 22 and 28 can be merged with the light passing through waveguide 24 also being utilized to measure the distance D.

Finally, the distal end of the apparatus 10 is connected to a photo detector and distance signal detector 30 which detects and measures the desired wavelengths and signals reflected back from the tympanic membrane 12. Preferably, detector 30 will include means for detecting the temperature of volume 19. As previously described, tympanic temperature measurement is well known.

A circuit 32 (shown schematically in FIG. 1) is provided for calculating the level of the constituent in the blood in response to a reduction in intensity of the testing light between the light generator 22 and the detector 30. The circuitry, through algorithms which will be described, compares the reduction in intensity with a reduction in intensity of the non-absorbable wavelength and with the measured distance D. In response to the measured variables, the circuit 32 calculates the glucose level in the blood in the tympanic membrane 12.

The circuit 32 includes a crystal oscillator 34 for driving the circuitry 32. Timing control circuitry 36 is provided for synchronizing the light generation and detection of the apparatus 10. A multiplexer 38 is provided for multiplexing the signals and light pulses to be generated by generators 22 and 28.

A signal preamplifier and demultiplexer 40 is provided for receiving the detected signals from detector 30 and amplifying and demultiplexing into individual signals representing the intensity of the reflected absorbable and non-absorbable wavelengths, the temperature of volume 19 and a signal to be used in calculating distance D. In the preferred embodiment, at least two light wavelengths (a wavelength absorbable by glucose and a reference wavelength not absorbable by glucose) are anticipated. However, in FIG. 1, up to N wavelengths are disclosed representing the utility of the apparatus for testing for multiple blood constituents and having multiple reference wavelengths. The first wavelength signal (for example, the testing light wavelength absorbable by glucose) is admitted to a first decoder 42. Other signal wavelengths (such as the reference wavelength not absorbable by glucose) is admitted to additional decoders such as decoder 44 (labeled decoder N in FIG. 1). A decoder 46 is also provided for decoding a signal representing the detection of the signal from the distance signal generator 28. The decoders place the demultiplexed signals in proper sequence.

All decoded signals are passed through filters 48-50 (for noise filtration) and subsequently through amplifiers 53-55. The amplified signals are passed through an analog-digital converter 56 to a microprocessor 58. Within the microprocessor 58, the signals are analyzed for the purposes of calculating the distance D and comparing the reduction in intensities between the absorbable wavelength and the non-absorbable wavelength for the purposes of determining the concentration of glucose within the blood in the tympanic membrane. A display 60 is provided for displaying to a healthcare provider the measured unknown (i.e., the blood glucose concentration).

It will be appreciated that circuitry for generating multiplexed infrared light and near-infrared light is well known. It will also be appreciated that circuitry and apparatus for measuring distances (such as distance D) through either ultrasonic or light measurements (including Doppler measurements) are well known. Also, it will be appreciated that apparatus and circuitry for detecting reflected light and demultiplexing signals are well known. Further, it will be appreciated that algorithms for calculating blood constituent levels in response to measured reductions in infrared light intensities are well known (see, e.g., U.S. Pat. No. 4,427,889).

The foregoing invention identifies structure and apparatus and a method of testing which eliminates certain of the disadvantages of the prior art. For example, multiple constituents may be tested through non-invasive testing by multiplexing a plurality of wavelengths which are selectively absorbable by the blood constituents to be measured. Alterative to multiplexing, the light can be evaluated through software algorithms.

The present technique also utilizes a temperature control circuit 62 for controlling the intensity of an infrared heater wavelength generated by generator 22. The temperature control circuitry 62 receives a signal from preamplifier 40 representing the temperature of volume 19 and tympanic membrane 12. In response to the signal, circuitry 62 controls generator 22 to heat and control the temperature of the tympanic membrane 12 and the auditory canal 18 to a sufficient elevated temperature to ensure that blood vessels within the tympanic membrane 12 remain open and that the measured absorption does not shift due to temperature change. As a result, the present apparatus and method have enhanced reliability over the prior art.

Importantly, the non-FTIR technique measures the exact distance D that light is traveling from its source to the sample and back to a detection apparatus. It will be recognized that in spectrophotometric methods, the control of a distance of the light path (to eliminate variability in the signal measurement) is essential since the reduction in intensity of the absorbable wavelength is a function of the distance it is traveling as well as the concentration of the constituent to be measured. Prior art apparatus for measuring blood glucose and other body constituents were not capable of measuring the actual light path distance which could vary from test to test. Instead, prior art apparatus had a fixed light path distance (see, for example, U.S. Pat. No. 4,014,321) or required the measurement of a so called "apparent" light path distance (see, for example, U.S. Pat. No. 4,805,623).

The foregoing description disclosed two principle aspects of the non-FTIR techniques: (1) a comparison of reduction in intensity between an absorbable and a non-absorbable wavelength and (2) the determination of the precise light path distance traveled by the absorbable and non-absorbable wavelengths. The utilization of these elements in combination with temperature control of the test area result in a blood constituent measurement device which is particularly suitable for non-invasive testing.

In the preferred example, the apparatus is carried on the distal end of a device to be inserted within the auditory canal of an ear. This will provide a simple, quick and accurate testing of blood glucose in a patient. However, certain of the salient features of the present invention (such as, the measurement of the precise distance and comparing reduction in intensity between non-absorbable and absorbable wavelengths) is also suitable for use in in vivo testing.

Figure 2:
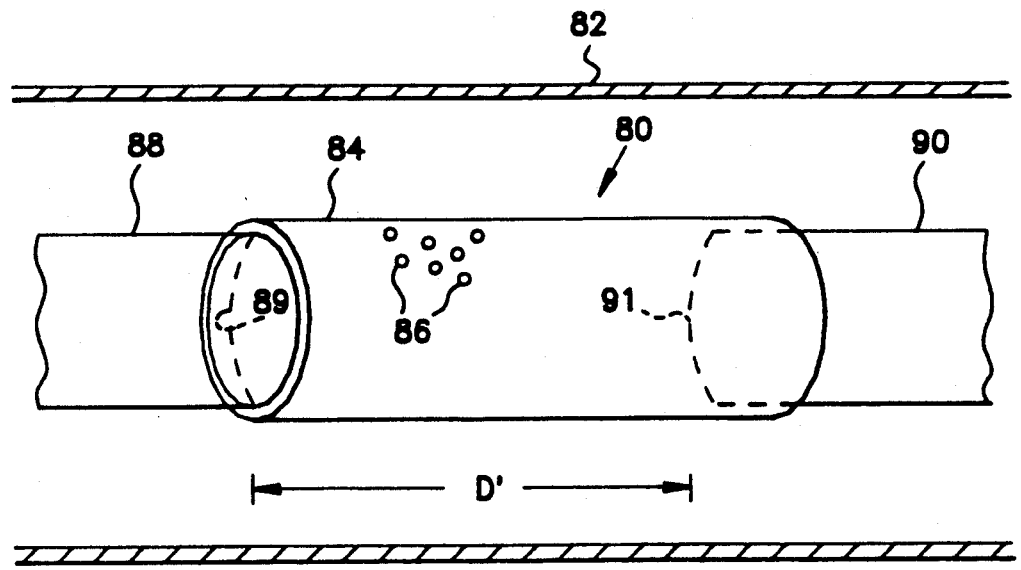
FIG. 2 is a view of an apparatus for use in invasive testing for blood glucose.

A particular structure for an in vivo application is shown in FIG. 2. In FIG. 2, a preferred apparatus 80 is shown inserted within a blood vessel 82. The apparatus 80, while shown in blood vessel 82, can be placed in any body cavity (e.g., the peritoneal cavity).

The apparatus 80 includes a generally cylindrical membrane 84. Preferably, membrane 84 is selected to be permeable to the blood constituent to be measured. In the case of measuring blood glucose, membrane 84 is preferably dialysis tubing having a molecular weight cutoff slightly greater than the molecular weight of glucose (i.e. greater than 180.16). To illustrate the permeability of membrane 84, holes 86 (shown greatly exaggerated in size) are provided passing through the membrane 84.

First and second waveguides 88 and 90 (preferably optical fibers) are provided inserted into opposite ends of membrane 84. The fibers can be press, fit and sealed in membrane 84. First waveguide 88 has a concave end 89 opposing a convex end 91 of second waveguide 90. Concave end 89 directs light toward end 91.

As in the previously described embodiment, multiplexed light wavelengths can be passed through waveguide 88 toward waveguide 90. The multiplexed wavelengths will include a wavelength absorbable by glucose and a non-absorbable wavelength. The absorbable and non-absorbable wavelengths pass through the membrane 84 between waveguides 88 and 90 and are passed from waveguide 90 to the circuitry (not shown) such as that shown and described in the aforementioned embodiment. When passing through the membrane 84, the intensities of both the absorbable and non-absorbable wavelengths will be reduced. The absorbable wavelength will be particularly reduced in response to the concentration of glucose within the membrane 84. By comparing the reduction in intensities between the absorbable and non-absorbable wavelength, the concentration of glucose within the membrane (and hence in the blood) can be determined if the distance D' between ends 89, 91 is known.

To measure distance D', an additional wavelength can be multiplexed with the absorbable and non-absorbable wavelength. The additional wavelength is selected to be passed from waveguide 88 toward waveguide 90 and reflected back from waveguide 90 as back reflection into waveguide 88. Through Doppler measurement techniques, the reflected light can be utilized to measure the accurate distance D' between waveguides 88 and 90. It will be appreciated that the phenomena of back reflection forms no part of this invention per se and can be accomplished through selecting particular wavelengths to reflect off of waveguide 90 or through the additional use of partially reflective coatings on surface 91. As a result of Doppler measuring the distance D' between waveguides 88 and 90, the present technique can compensate for distance variations between waveguides 88 and 90 which may result from compression due to posture of the patient, thermal expansion, manufacturing tolerances and other causes.

Figure 3:
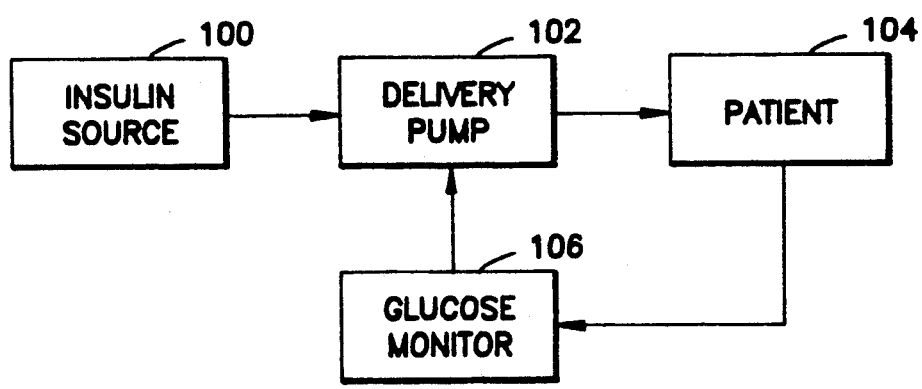
FIG. 3 is a schematic view of a system using the apparatus to control admission of a drug to a patient.

The use of the in vivo apparatus 80 is particularly suitable for constantly monitoring the blood constituent level of a patient. Continuous monitoring is desireable during surgical procedures. Also, continuous monitoring permits feedback control of chemical administration to patients. For example, with reference to FIG. 3, it is schematically shown how the present technique can be utilized to control the administration of insulin to a patient. In FIG. 3, an insulin source 100 is shown connected via a delivery pump 102 to a patient 104. The apparatus of the present apparatus 106 (which includes the apparatus 80 plus the circuitry of FIG. 1 or just the entire apparatus 10 of FIG. 1) is shown connected to the patient 104 to constantly monitor the blood glucose of the patient. The measured blood glucose level of the patient as monitored by the present invention 106 is utilized to control the action of the delivery pump 102 in order to maintain the patient's blood glucose within predetermined tolerances of a desired blood glucose level.

B. FTIR Apparatus

The foregoing discussion pertains to use of spectrometry in a non-FTIR application (i.e., an application utilizing other than techniques known in Fourier transform infrared spectrometry). However, the concepts disclosed in the prior discussion (namely the use of the ear drum or tympanic membrane as a target for spectral analysis of blood constituents) may be applicable to use in an FTIR application.

FIG. 4 is a schematic representation of an FTIR spectrometry apparatus for use in testing blood constituents. The apparatus, as will be more fully described, utilizes a body tissue as a target and as a moving reflecting mirror in the FTIR process. In a preferred embodiment, this concept is disclosed using the ear drum as the tissue which is the moving mirror in the FTIR process. In a preferred embodiment, the apparatus is shown for use in an non-invasive embodiment. However, it will be appreciated by those skilled in the art that the concept of utilizing a body tissue as the moving mirror in an FTIR process need not be limited to a tympanic membrane in a non-invasive embodiment, but may also utilize other body tissue as the moving target, whether invasive or non-invasive.

Referring now to FIG. 4, an FTIR apparatus is shown in a schematic format. The apparatus is contained within a housing 200 which is sized to be snugly received in the auditory canal 202 of the human ear and opposing tympanic membrane 204. The ear drum 204, auditory canal 202 and housing 200 seal off a portion of the auditory canal 202 to define a test chamber 206. In this respect, the housing 200 is similar to the apparatus 16 as shown in the embodiment in FIG. 1. Contained within the apparatus 200 is a source (such as a tube) 208 for admitting or removing a flow 210 of air into or from the chamber 206 to move or modulate the tympanic membrane 204.

A light source 212 is provided for generating a beam 214 of light which includes wavelengths absorbable by the constituents of interest (for example glucose) contained within the tympanic membrane 204. Preferably, light beam 214 is a broad spectral beam to allow absorption analysis at different wavelengths as will be described.

The apparatus also includes a beam splitter 216 for splitting the light beam 214 into a reference beam 218 and a test beam 220. The test beam 220 is directed toward the tympanic membrane 204. The reference beam 218 is reflected off of a fixed position mirror 222 toward a light detector 224. The housing 200 also contains distance measurer 226 and an infrared heater 228 which serve the function and purpose as the distant signal generator 28 and infrared heater 22 (together with warming temperature control 62) of the embodiment of FIG. 1.

In both the FTIR and non-FTIR embodiments described in this application, an infrared heater (heater 228 in FIG. 4 and the heater coupled with source 22 in FIG. 1) is used to control the temperature during measurement. While a separate infrared heater is shown in the preferred embodiment, the use of a separate heater may be avoidable by controlling the energy or load of the infrared light sources. Namely, the energy from the infrared light sources may be sufficient to warm the ear area. By simply measuring or monitoring the temperature, the duty cycle of the light sources may be varied to control the temperature. In such case, a separate infrared heater would be unnecessary.

With the apparatus as shown and described, light which is reflected off the tympanic membrane 204 results in a modified beam 230 of light where certain of the wavelengths of the test beam 220 have been absorbed by the constituents within the tympanic membrane 204. The amount of absorption and the wavelengths at which the absorption occurs is indicative of the types and amounts of constituents present in the blood within the tympanic membrane 204. The modified light 230 is received at the detector 224 together with the reference beam 218 reflected off of mirror 222. The modified beam 230 and the reference beam 218 interact to form an interference pattern which is measured and detected by detector 224 to generate a signal which is received and processed by a main processor 240. The processor determines the constituent level in response to the interference pattern. It will be appreciated the processes for performing such an analysis form no part of this invention per se and are known in the art. For example, the aforementioned article of Arnold and Small describes a procedure for using FTIR technology to determine glucose levels in a sample.

With the present apparatus as shown in FIG. 4, the tympanic membrane can be utilized as the moving mirror by injecting or removing air through air source 208 to increase or decrease air pressure within chamber 206. This will result in movement of the tympanic membrane 204. Hence, the tympanic membrane 204, while moving and reflecting beam 230 back to detector 224, becomes the moving mirror in an FTIR system.

The present apparatus has numerous advantages in that it is full-spectrum permitting a test for interference wavelengths over many wave bands. As a result, many constituents can be simultaneously tested and different points of absorption for a particular wave constituent spectra can be tested.

It is recognized in FTIR systems it is necessary to control and know the distance from the light source to the mirror as well as controlling temperature. To effect these controls, the infrared heater 228 is provided and distance measure 226 is provided, the structure and function of which having been previously described with reference to the previous embodiments of FIG. 1.

By gradually increasing and/or decreasing air pressure within the auditory canal, the tympanic membrane moves and becomes one axis of the interferogram generator system in the FTIR spectrometer. The other axis of the interferometer system is provided by the split beam reflected off of the stationary mirror 222. The full system permits the generation of a signal averaged, high resolution full-spectral scan. This permits the detection and quantification of many compounds of biological interest through both non-invasive and invasive testing as well as continuous testing to provide a continuous signal indicating changes in constituent levels. The latter would be particularly useful to monitor constituents during procedures such as surgery.

FIG. 5 shows modified use of FTIR technology with invasive testing. The reader will recognize the embodiment of FIG. 5 being similar to that of FIG. 2. Accordingly, similarly numbered elements are numbered identically in FIG. 5 except for the addition of the extra prime ('). As shown in FIG. 5, the apparatus 80' includes a generally cylindrical membrane for defining a cylindrical chamber 84'. The chamber 84' is preferably selected to be permeable to the blood constituents to be measured. In the case of measuring blood glucose, the chamber 84' is preferably a dialysis tubing within a molecular weight cutoff slightly greater than the molecular weight of glucose. To illustrate the permeability of the chamber 84', the whole of 86' (shown greatly exaggerated in size) is provided passing through the membrane of chamber 84'. In a preferred embodiment, the apparatus 80' is shown inserted within a blood vessel 82'. It will be appreciated that the apparatus 80' could be placed in any body cavity.

A first waveguide (preferably an optical fiber) 88' is inserted within one end of the chamber 84' and terminates at preferably a flat end 89'. End 89' opposes a membrane 91' (at least partially reflective) disposed at an opposite end of chamber 84'. The flat axial membrane 91' is movable relative to the end 89'. For example, the membrane 91' may be vibrated through ultrasonic application. Also, membrane 91' could be a piezoelectric film and a charge across the membrane 91' could be varied to move the film 91'. Alternatively, the apparatus 80' could simply be placed against an artery with the membrane 91' flexing and moving in response to blood pulsing through the artery. With this structure, the membrane 91' becomes the moving mirror in an FTIR application. The distance D" can be measured in a manner similar to the measurement of distance D' in the embodiment of FIG. 2. The membrane 91' reflects light back through waveguide 88' to provide an interferogram with a previously split off reference beam.

In several embodiments discussed in this application, the tympanic membrane was used as a target or a moving mirror. The use of the tympanic membrane as a target or as a moving mirror in testing for blood constituents has many advantages. The tympanic membrane is very thin, which aids in calculating or knowing the path length traveled by the light source. Also, the tympanic membrane contains both tissue fluid and whole blood. This makes for a better sample. The tympanic membrane is highly vascular and receives a constant blood flow even when a patient is injured or sick. There is little bone or fat within the tympanic membrane thereby providing a simple matrix. Also, the membrane is generally planar and reflective, which aids in spectrometric analysis. The membrane is accessible and temperature controllable. Also, the ear canal can be readily closed to provide an enclosed test area. Finally, the membrane is movable to permit its use as a moving mirror in an FTIR application.

Through the foregoing detailed description of the present invention, it has been shown how the objects of the present invention have attained in a preferred manner. However, modifications and equivalents of the disclosed concepts, such as those which would readily occur to one skilled in the art, are intended to be included within the scope of the claims of the present invention.

What is claimed is:

1. An apparatus for determining a level of a constituent in a body fluid contained within a body tissue, said apparatus comprising:

light generating means for generating a beam of a source light including at least one wavelength absorbable by said constituents;

light detecting means for receiving light and measuring an intensity of said light;

beam splitting and directing means for splitting said source beam into at least a reference beam and a test beam with said reference beam directed toward said light detecting means and with said test beam directed toward said tissue for said test beam to be modified by at least partial absorption of said at least one wavelength by said constituent within said tissue and with said modified light reflected off said tissue toward said light detecting means, said modified light and said reference light at said light detecting means cooperating to generate an interference pattern corresponding at least in part to a level of said constituent within said tissue;

processing means for receiving an output of said light detecting means and calculating said level of said constituent in response to said output.

2. An apparatus according to claim 1 comprising means for moving said tissue to vary an angle between said tissue and said light source.

3. An apparatus according to claim 1 comprising means for measuring a distance from said apparatus to said tissue.

4. An apparatus according to claim 1 comprising means for controlling a temperature of said tissue.

5. An apparatus according to claim 1 wherein said constituent is glucose.

6. An apparatus according to claim 1 wherein said light generating means, said light detecting means said beam splitting and directing means and said processing means are elements of a Fourier transform infrared spectrometry apparatus having said tissue as a moving mirror for said apparatus.

7. An apparatus for determining a level of a constituent in a body fluid contained within a tympanic membrane, said apparatus comprising:

light generating means for generating a beam of a source light including at least one wavelength absorbable by said constituents;

light detecting means for receiving light and measuring an intensity of said light;

beam splitting and directing means for splitting said source beam into at least a reference beam and a test beam with said reference beam directed toward said light detecting means and with said test beam directed toward said membrane for said test beam to be modified by at least partial absorption of said at least one wavelength by said constituent with said membrane and with said modified light reflected off said membrane toward said light detecting means, said modified light and said reference light at said light detecting means cooperating to generate an interference pattern corresponding at least in part to a level of said constituent within said membrane;

processing means for receiving an output of said light detecting means and calculating said level of said constituent in response to said output.

8. An apparatus according to claim 7 comprising means for moving said membrane to vary an angle between said membrane and said light source.

9. An apparatus according to claim 7 comprising means for measuring a distance from said apparatus to said membrane.

10. An apparatus according to claim 7 comprising means for controlling a temperature of said membrane.

11. An apparatus according to claim 7 wherein said constituent is glucose.

12. An apparatus to claim 7 wherein said light generating means, said light detecting means, said beam splitting and directing means and said processing means are elements of a Fourier transform infrared spectrometry apparatus having said membrane as a moving mirror for said apparatus.

* * * * *